(12) United States Patent
Nakamura et al.

(10) Patent No.: US 9,300,883 B2
(45) Date of Patent: Mar. 29, 2016

(54) IMAGING DEVICE, IMAGE PROCESSING METHOD FOR IMAGE CAPTURED BY IMAGING DEVICE, AND IMAGING SYSTEM

(75) Inventors: Toru Nakamura, Oyama (JP); Koji Hayafune, Suginami-ku (JP); Akira Higuchi, Meguro-ku (JP)

(73) Assignee: EXAMASTICA CO., Tokyo (JP)

( * ) Notice: Subject to any disclaimer, the term of this patent is extended or adjusted under 35 U.S.C. 154(b) by 380 days.

(21) Appl. No.: 13/882,972

(22) PCT Filed: Nov. 1, 2011

(86) PCT No.: PCT/JP2011/075141
§ 371 (c)(1),
(2), (4) Date: May 1, 2013

(87) PCT Pub. No.: WO2012/060353
PCT Pub. Date: May 10, 2012

(65) Prior Publication Data
US 2013/0222560 A1    Aug. 29, 2013

(30) Foreign Application Priority Data
Nov. 5, 2010    (JP) .................................. 2010-248342

(51) Int. Cl.
*H04N 7/18* (2006.01)
*H04N 5/33* (2006.01)
*A61B 5/00* (2006.01)
*A61B 5/22* (2006.01)
(Continued)

(52) U.S. Cl.
CPC ................ *H04N 5/33* (2013.01); *A61B 5/0059* (2013.01); *A61B 5/228* (2013.01); *G01N 1/286* (2013.01);
(Continued)

(58) Field of Classification Search
USPC ............. 348/61, 49, 50, 68, 89, 33, 130, 131, 348/135, 164, 169, 180, 231.3, 270, 297, 348/342, 370, 673, 687, 714, 725, 759, 348/835; 250/204, 203.2, 330, 338.1, 365, 250/372, 559.04, 559.16; 382/103, 106, 382/154, 260, 274, 291; 356/10, 51, 927
See application file for complete search history.

(56) References Cited

U.S. PATENT DOCUMENTS 5,966,204 A    10/1999  Abe
2002/0051578 A1*   5/2002  Imagawa et al. .............. 382/224
(Continued)

FOREIGN PATENT DOCUMENTS

JP    10-020198 A    1/1998
JP    2000-131223 A    5/2000
(Continued)

OTHER PUBLICATIONS

International Search Report (PCT/ISA/210) issued on Jan. 10, 2012, by the Japanese Patent Office as the International Searching Authority for International Application No. PCT/JP2011/075141.

*Primary Examiner* — Jefferey Harold
*Assistant Examiner* — Mustafizur Rahman
(74) *Attorney, Agent, or Firm* — Buchanan Ingersoll & Rooney PC

(57) ABSTRACT

An imaging device for capturing an image of an imaging object that is an artificial food mass, in which a light-transmissive microparticle is contained in a base material having a property of blocking infrared light, includes imaging means for capturing the image of the imaging object from one side; and an infrared light source that emits infrared light on the imaging object from the other side of the imaging object. The imaging means includes visible-light removing means for not receiving visible light. The imaging means captures the image of the imaging object while the infrared light source emits the infrared light on the imaging object. The device can accurately count the number of "microparticles not finely crushed or ground" by a computer or the like.

9 Claims, 15 Drawing Sheets

(51) Int. Cl.
   *G01N 21/3563*  (2014.01)
   *G01N 1/28*  (2006.01)
   *H04N 5/225*  (2006.01)
   *G01N 15/14*  (2006.01)

(52) U.S. Cl.
   CPC ........ *G01N 15/1463* (2013.01); *G01N 21/3563* (2013.01); *H04N 5/2256* (2013.01); *G01N 2015/1486* (2013.01); *G01N 2015/1497* (2013.01)

(56) References Cited

U.S. PATENT DOCUMENTS

| | | | | |
|---|---|---|---|---|
| 2005/0033184 | A1* | 2/2005 | Christoph | 600/476 |
| 2005/0168627 | A1* | 8/2005 | Yi et al. | 348/373 |
| 2006/0071156 | A1* | 4/2006 | Masaki | 250/226 |
| 2007/0148535 | A1* | 6/2007 | Nagai et al. | 429/96 |
| 2007/0201738 | A1* | 8/2007 | Toda et al. | 382/144 |
| 2009/0093727 | A1* | 4/2009 | Sato | 600/476 |
| 2009/0128508 | A1* | 5/2009 | Sohn et al. | 345/173 |
| 2009/0290864 | A1* | 11/2009 | Asakura et al. | 396/382 |
| 2009/0312671 | A1* | 12/2009 | Miura | 600/590 |
| 2012/0002042 | A1 | 1/2012 | Okuma | |

FOREIGN PATENT DOCUMENTS

| | | |
|---|---|---|
| JP | 2001-074670 A | 3/2001 |
| JP | 4652480 B1 | 3/2011 |
| WO | WO 2008/020588 A1 | 2/2008 |

\* cited by examiner (a)

(b)

(a)

(b)

(a)

(b)

(a)

(b)

(a)

(b)

(a)

(b)

IMAGING DEVICE, IMAGE PROCESSING METHOD FOR IMAGE CAPTURED BY IMAGING DEVICE, AND IMAGING SYSTEM

TECHNICAL FIELD

The present invention relates to an imaging device that, when the masticatory function of a human is evaluated by using an artificial food mass containing microparticles, captures an image by using infrared radiation for counting the number of microparticles contained in the artificial food mass masticated by the human, by a computer or the like. The present invention also relates to an image processing method for the image captured by the imaging device, and to an imaging system.

BACKGROUND ART

Masticating, that is, an action including chewing and crushing food, mixing well the food with saliva, making a wet mass of food with a proper size, and preparing to be swallowed is necessary when a human eats a solid. Masticating also provides a waking effect and a relaxing effect; prevents obesity, dementia, a decrease in vision, distortion in posture, a cavity, a cancer, etc.; and provides an effect of restricting a change with age by an increase in volume of blood in the brain.

This masticatory ability (masticatory efficiency) is affected by many conditions, such as the number of teeth, whether teeth being healthy or not, occlusal form, periodental condition, jaw shape, masticatory muscle strength, mandibular motion pattern, age, and prosthesis condition.

A method of evaluating the masticatory ability may be, for example, a method in which a peanut or a raw rice is masticated by a human a predetermined number of times and the condition of the masticated peanut or rice is observed (screening method) or a method in which a color changeable chewing gum is masticated by a human a predetermined number of times and a change in color of the masticated gum is observed (color changeable gum method).

However, the screening method has low reproducibility, and the measurement time takes about 24 hours. Also, the observation result of the color changeable gum method cannot be quantified, and this method does not observe the masticatory ability, but actually observes the mixing ability.

Owing to this, the inventors and others of the present invention have developed an artificial food mass containing "microparticles that are in a substantially uniform spherical shape and have a property of being finely crushed and ground by masticating" and a system that evaluates the masticatory function by using this artificial food mass (PTL 1).

The system for evaluating the masticatory function includes a step of allowing a human to masticate an artificial food mass containing microparticles that are finely crushed and ground by masticating and have a spherical shape unless the microparticles are masticated; a step of enlarging the artificial food mass masticated by applying pressure to a proper thickness with which the microparticles are not pressed and crushed while sandwiching the masticated artificial food mass between two preparation sheets; and a step of counting the number of microparticles retaining the spherical shape that remain in the artificial food mass enlarged between the two preparation sheets by applying the pressure.

With this method, the number of "particles not finely crushed or ground" can be counted without using an organic solvent or expensive equipment for evaluation.

CITATION LIST

Patent Literature

PTL 1: International Publication No. WO 2008/020588

SUMMARY OF INVENTION

Technical Problem

However, to accurately count the number of "particles not finely crushed or ground," a human has conventionally counted the number through a visual check. Hence, the person has had to take a long time and be well experienced for counting the number of microparticles.

If a computer or the like automatically counts the number of "particles not finely crushed or ground," an image of a masticated artificial food mass is required to be captured by a CCD (charge coupled device image sensor) camera or the like while the masticated artificial food mass is sandwiched between two preparation sheets, and the number of microparticles is required to be counted by means of pattern matching or the like.

However, the difference between the color of the artificial food mass and the color of the microparticles may not be clear or the profiles of the microparticles may not be clearly captured. With the conventional method, it has been difficult to accurately count the number of "microparticles not finely crushed or ground" by the computer or the like.

In particular, if components equivalent to components of a commercially available chewing gum are used for the artificial food mass in view of food safety, various components are contained as a sweetener due to the necessity in a manufacturing process for the chewing gum, resulting in that the image may be unclear when the various components are recognized by the computer.

Further, during the image capture, if environmental light, such as the sunlight or light of a fluorescent lamp, enters the CCD camera or the like, the contrast of the captured image may be decreased, resulting in that the recognition accuracy of the computer or the like may be decreased.

Also, to block such environmental light, if the preparation sheets sandwiching the masticated artificial food mass or the imaging device such as the CCD camera is covered with a case or a black cloth, operability during the image capture may be decreased.

In the light of situation, an object of the present invention is to provide an imaging device for capturing an infrared image, the device which can accurately count the number of "microparticles not finely crushed or ground" even by a computer or the like, by emitting infrared light on an artificial food mass that is an imaging object during image capture, and by capturing an image of the infrared light passing through the artificial food mass by the imaging device.

Further, another object of the present invention is to provide an image processing method capable of causing the shape of the microparticle to be clear in the captured image, and an imaging system that performs a process from the image capture to the image processing.

Solution to Problem

The present invention is made to address the problems in the prior art and to attain the objects, and an imaging device according to the present invention is for capturing an image of an imaging object that is an artificial food mass, in which a light-transmissive microparticle is contained in a base material having a property of blocking infrared light. The device includes imaging means for capturing the image of the imaging object from one side; and an infrared light source that emits infrared light on the imaging object from the other side of the imaging object. The imaging means includes visible-light removing means for not receiving visible light. The imaging means captures the image of the imaging object while the infrared light source emits the infrared light on the imaging object.

The imaging device according to the present invention includes a diffusing filter for decreasing unevenness of the infrared light emitted from the infrared light source, the diffusing filter being provided between the infrared light source and imaging object means.

Also, in the imaging device according to the present invention, the infrared light source includes a light guide panel for uniformly guiding the infrared light emitted from the infrared light source.

Also, in the imaging device according to the present invention, the visible-light removing means is a visible-light cut filter provided at an object side of the imaging means.

Also, in the imaging device according to the present invention, the imaging object is located above the infrared light source and below the imaging means while the imaging object is sandwiched between preparation sheets.

Also, in the imaging device according to the present invention, the artificial food mass is a chewing gum.

Also, an imaging method according to the present invention is for capturing an image of an artificial food mass, in which a light-transmissive microparticle is contained in a base material having a property of blocking infrared light, by any one of the above-described imaging devices. The method includes, after the artificial food mass is masticated by a human a predetermined number of times, emitting the infrared light from the infrared light source on the artificial food mass from one side of the artificial food mass, and capturing the image of the artificial food mass by the imaging means from the other side of the artificial food mass, while the artificial food mass is sandwiched between the preparation sheets.

Also, an imaging method according to the present invention includes, after the chewing gum is masticated by a human a predetermined number of times, removing various components by using a various-component removing method for removing the various components contained in the chewing gum; and emitting the infrared light from the infrared light source on the artificial food mass from one side of the artificial food mass, and capturing the image of the artificial food mass by the imaging means from the other side of the artificial food mass, while the chewing gum is sandwiched between the preparation sheets.

Also, in the imaging method according to the present invention, the various-component removing method is one of kneading in warm water and sandwiching between cooking sheets for a predetermined time.

Also, an image processing method according to the present invention is for causing a shape of the microparticle to be clear in the image of the imaging object captured by any one of the above-described imaging devices. The method includes a step of performing a mathematic operation on image data and generating brightness-standardized image data so that a brightness of the captured image data becomes close to a brightness of predetermined model image data; a step of performing a mathematic operation on the brightness-standardized image data and generating contrast-standardized image data so that a contrast of the brightness-standardized image data becomes close to a contrast of the model image data; a step of calculating a brightness distribution of the contrast-standardized image data, performing a mathematic operation on the contrast-standardized image data, and generating enhanced image data so that a brightness of a region indicative of the microparticle is increased in the brightness distribution; and a step of applying a band-pass filter, in which a brightness of an edge portion of the microparticle is a threshold, to the enhanced image data, and generating count image data.

Also, in the image processing method according to the present invention, the microparticle includes a plurality of microparticles, and the number of the microparticles in the count image data is counted by comparing the count image data with pattern image data indicative of a shape of the microparticle.

Also, the image processing method according to the present invention includes a simple comparison step of comparing only a predetermined number of pixels in a region indicative of the shape of the microparticle in the pattern image data and a predetermined number of pixels outside the region indicative of the shape of the microparticle, with the count image data; and a complete comparison step of comparing all pixels in the pattern image data with the count image data if a result of the simple comparison step exceeds a predetermined correspondence ratio.

An imaging system according to the present invention is an image processing system and includes any one of the above-described imaging devices; and an image processing device for processing image data of the imaging object captured by the imaging device. The image processing device includes a storage device for saving the image data captured by the imaging device, and an arithmetic device for processing the image data saved in the storage device. The image processing device performs a mathematic operation on the image data and generates brightness-standardized image data so that a brightness of the captured image data becomes close to a brightness of predetermined model image data; performs a mathematic operation on the brightness-standardized image data and generates contrast-standardized image data so that a contrast of the brightness-standardized image data becomes close to a contrast of the model image data; calculates a brightness distribution of the contrast-standardized image data, performs a mathematic operation on the contrast-standardized image data, and generates enhanced image data so that a brightness of a region indicative of the microparticle is increased in the brightness distribution; and applies a band-pass filter, in which a brightness of an edge portion of the microparticle is a threshold, to the enhanced image data, and generates count image data.

Also, in the imaging system according to the present invention, the microparticle includes a plurality of microparticles, and the number of microparticles in the count image data is counted by comparing the count image data with pattern image data indicative of a shape of the microparticle.

Also, in the imaging system according to the present invention includes: a simple comparison step of comparing only a predetermined number of pixels in a region indicative of the shape of the microparticle in the pattern image data and a predetermined number of pixels outside the region indicative of the shape of the microparticle, with the count image data; and a complete comparison step of comparing all pixels in the pattern image data with the count image data if a result of the simple comparison step exceeds a predetermined correspondence ratio.

Advantageous Effects of Invention

With the present invention, when the image of the imaging object is captured, the infrared light that is emitted on the imaging object and passes through the imaging object is captured. Accordingly, the image with a high contrast between the artificial food mass and the microparticle can be captured without being affected by environmental light.

Further, with the present invention, the image processing is performed on the captured infrared image with the high contrast. Accordingly, the image with a further clear difference between the artificial food mass and the microparticle can be generated.

Further, with the present invention, even if the number of microparticles in the imaging object is counted, since the image with the clear difference between the artificial food mass and the microparticle is used and the shape of the microparticle is clear, the number of microparticles can be accurately and quickly counted even by a computer etc.

BRIEF DESCRIPTION OF DRAWINGS

FIG. 8(a) is an illustration expressing a brightness distribution (histogram) for model image data. FIG. 8(b) is an illustration expressing a brightness distribution (histogram) for captured infrared image data.

FIG. 9(a) is an illustration expressing a brightness distribution (histogram) for model image data. FIG. 9(b) is an illustration expressing a brightness distribution (histogram) for brightness-standardized infrared image data.

FIG. 10(a) is an illustration showing an example of a high-pass filter. FIG. 10(b) is an illustration showing an example of a binarizing filter.

DESCRIPTION OF EMBODIMENTS

A mode for implementing the present invention (embodiment) is described in more detail below with reference to the drawings.

Figure 1:
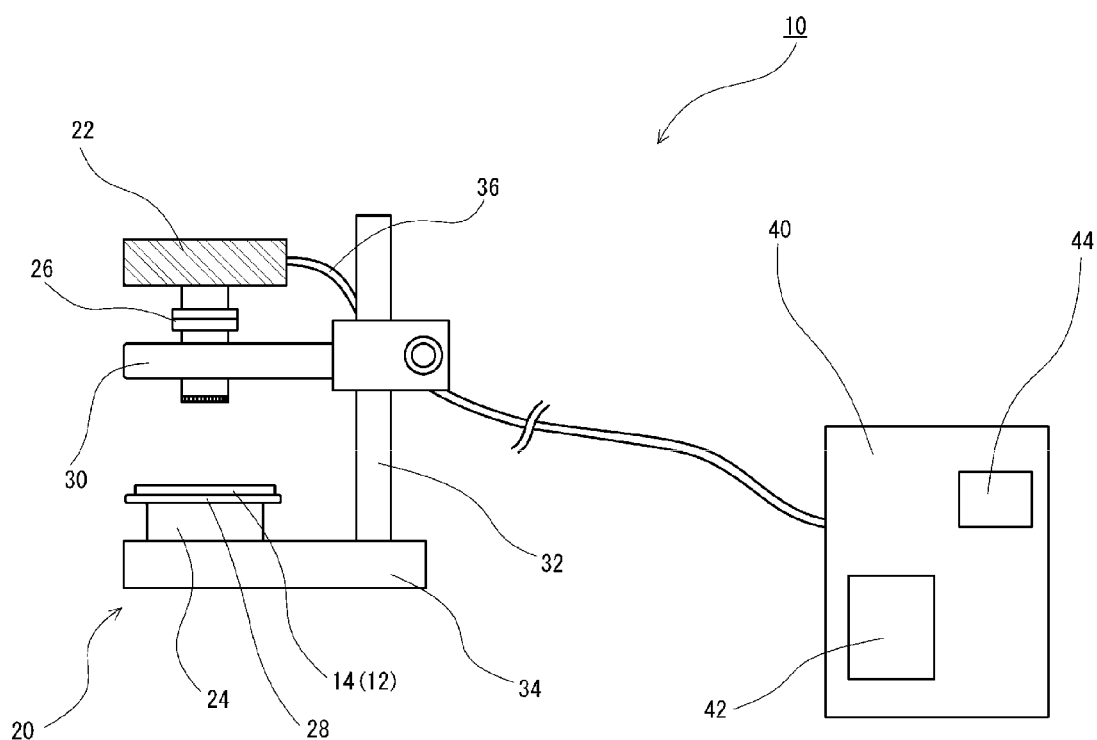
FIG. 1 is a brief configuration diagram for explaining a configuration of an imaging system of the present invention.
Figure 2:
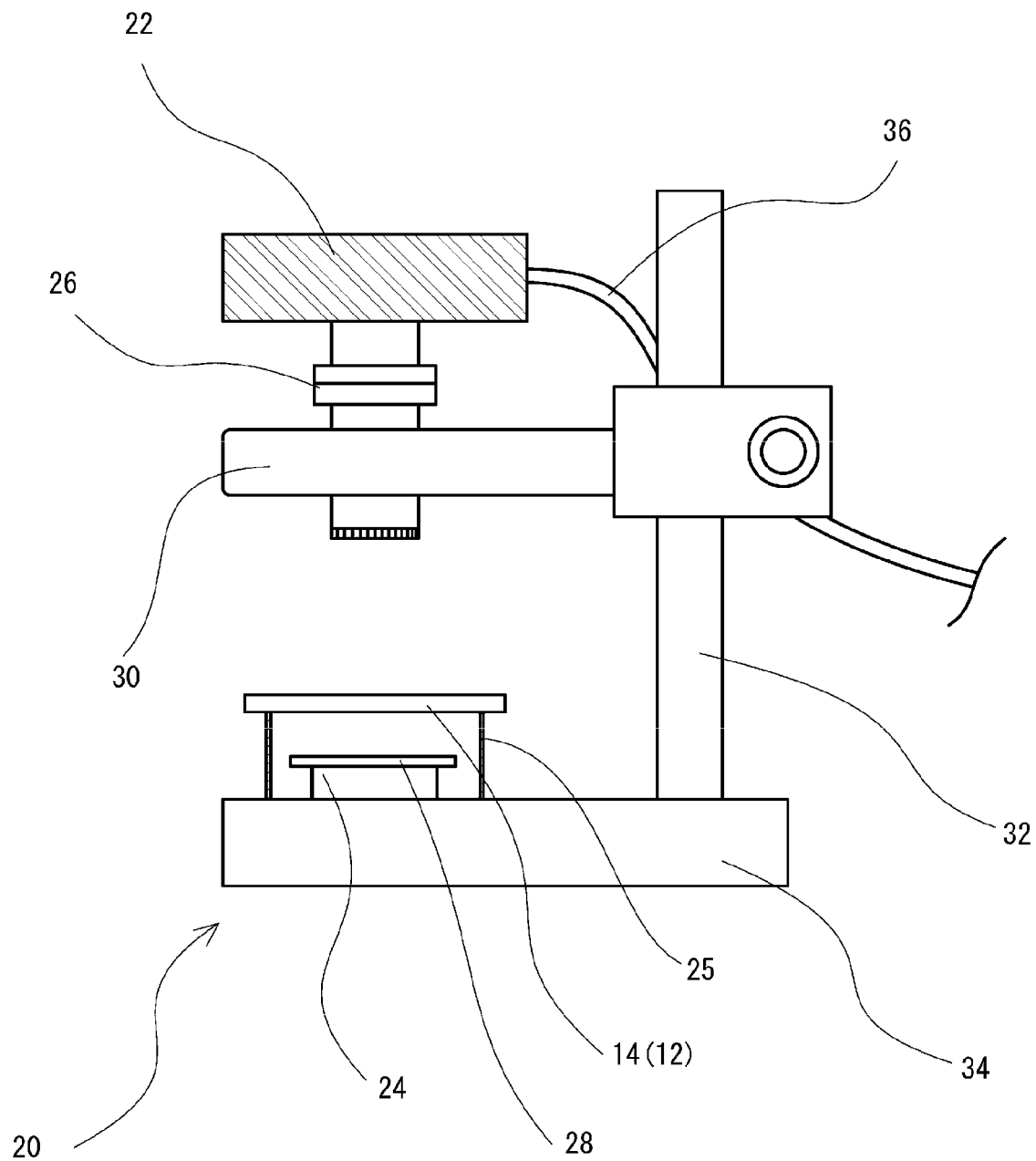
FIG. 2 is a brief configuration diagram for explaining a configuration of an imaging device.
Figure 3:
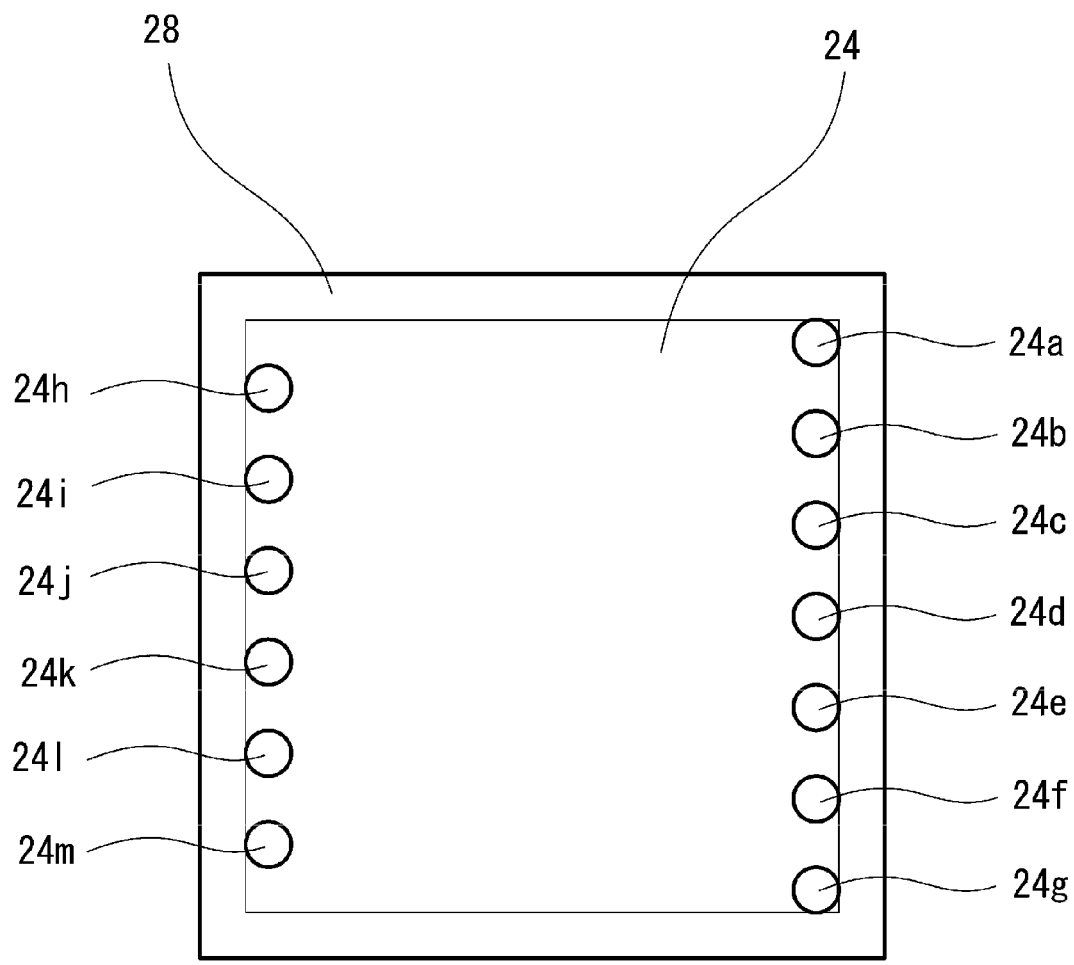
FIG. 3 is a brief configuration diagram for explaining a positional relationship between light source portions 24a to 24m of an infrared light source 24 and a diffusing filter 28.
Figure 4:
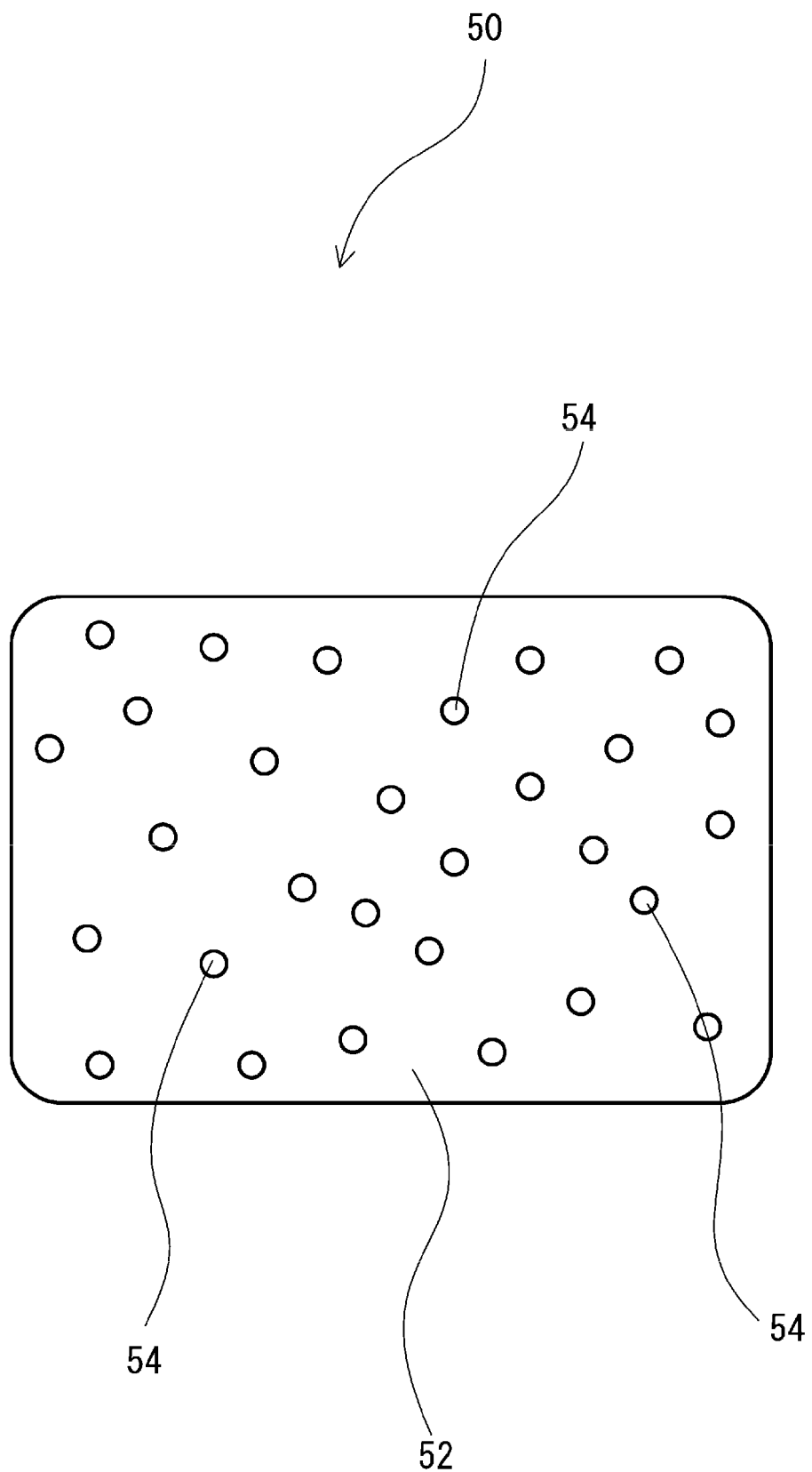
FIG. 4 is a brief configuration diagram for explaining a shape of a chewing gum being an example of an imaging object, an image of which is captured by the imaging system of the present invention.

FIG. 1 is a brief configuration diagram for explaining a configuration of an imaging system of the present invention. FIG. 2 is a brief configuration diagram for explaining a configuration of an imaging device. FIG. 3 is a brief configuration diagram for explaining a shape of a chewing gum being an example of an imaging object, an image of which is captured by the imaging system of the present invention. FIG. 4 is a brief configuration diagram for explaining a state in which the chewing gum in FIG. 3 is pressed by preparation sheets for capturing the image of the chewing gum by the imaging system.

As shown in FIG. 1, an imaging system 10 of the present invention includes an imaging device 20 that captures an image of an imaging object 12, and a computer 40 that is an image processing device for performing image processing on captured infrared image data.

As shown in FIG. 2, the imaging device 20 of this embodiment includes imaging means 22 for capturing an image of preparation sheets 14 with the imaging object 12 sandwiched therebetween from an upper side of the preparation sheets 14, and an infrared light source 24 that emits infrared light from a lower side of the preparation sheets 14. FIG. 2 shows a mount table 25 in a sectional view for explanation. The preparation sheets 14 are mounted on the mount table 25.

The imaging means 22 is not particularly limited as long as the imaging means can capture an image of the preparation sheets 14 at a close position. For example, a film camera, or a digital camera using an element, such as a CCD (charge coupled device image sensor) or a CMOS (complementary metal oxide semiconductor), may be used. In particular, if an image of an imaging object is captured and then image processing is performed, a digital camera is preferably used. Also, the imaging means 22 may capture not only a still image but also a movie.

Also, if such imaging means 22 captures an image of an imaging object, an angle of view may be set so that a square range measuring 10 μm per side of the imaging object serves as one pixel. If the angle of view is set in this way, microparticles contained in the imaging object can be clearly recognized.

In this embodiment, although described later, microparticles 54 contained in an artificial food mass 50 serving as an imaging object each have a diameter in a range from about 250 to 300 μm, and hence image capture is performed while the square range measuring 10 μm per side serves as one pixel. However, the angle of view may be properly set in accordance with the size of the microparticles 54.

Also, if the imaging means 22 has a high resolution, finer image capture may be performed. For example, image capture may be performed while a square range measuring 5 μm per side serves as one pixel, or image capture may be performed while a square range of 1 μm per side serves as one pixel.

If an image of an imaging object is captured by a plurality of image capture steps, a CCD camera with about 2 million pixels may be used. If an image of an imaging object is captured by a single image capture step, a CCD camera with about 9 million pixels is preferably used.

Also, a visible-light cut filter 26 is provided as visible-light removing means for transmitting only light in the infrared region and cutting visible light, at an object side of the imaging means 22. The visible-light cut filter 26 is not particularly limited as long as the filter transmits infrared light which is described later. For example, a filter with a property of transmitting light with wavelengths of 700 nm or longer, or a filter with a property of transmitting only light with wavelengths in a range from 700 nm to 4 μm may be used.

In this embodiment, the visible-light cut filter 26 is used so that the imaging means does not receive visible light. For example, the imaging means 22 that includes visible-light removing means, that does not receive visible light, and that can receive only infrared light (infrared radiation), such as an infrared camera, may be used.

Also, the infrared light source 24 is not particularly limited as long as the infrared light source can emit infrared light. For example, an infrared light source 24 using a LED (light emitting diode) or a halogen lamp may be used. Also, a light source having a light-quantity adjusting function is preferably used so that the light quantity can be adjusted during image capture.

The infrared light (infrared radiation) that is emitted by the infrared light source 24 may preferably use infrared radiation in a range from near-infrared radiation to middle infrared radiation with wavelengths in a range from about 700 nm to 4 μm, with regard to properties of infrared radiation as heat waves.

Also, if a light source having a plurality of LEDs arranged therein is used, as shown in FIG. 2, a diffusing filter 28 is preferably provided between the infrared light source 24 and the preparation sheets 14, to reduce unevenness of the emitted light.

Alternatively, instead of the diffusing filter 28, a light guide panel, such as a Meibi panel manufactured by Meiko Kasei Co., Ltd., which can evenly guide the light emitted by the infrared light source 24, may be used.

To restrict the unevenness of the diffusing filter 28 or the light guide panel, as shown in FIG. 3, light source portions 24a to 24m of the infrared light source 24 are preferably arranged at both ends of the diffusing filter 28 or the light guide panel and preferably emit infrared light from both the opposing ends.

Reference sign 30 denotes holding means for fixing the imaging means at a predetermined height. Reference sign 32 denotes a support shaft to which the holding means 30 is fixed. Reference sign 34 denotes a base portion on which the infrared light source 24 etc. is mounted. Reference sign 36 denotes a cable for connection with the computer 40.

The computer 40 of this embodiment includes a storage device 42 and an arithmetic device 44. Infrared image data captured by the imaging means is transmitted to the computer through the cable and stored in the storage device.

Hereinafter, a case in which an artificial food mass containing "substantially uniform spherical microparticles having a property of being finely crushed and ground by masticating" is described as an example of the imaging object 12, an image of which is captured by the imaging system 10.

As shown in FIG. 4, the artificial food mass 50 of this embodiment uses components equivalent to those of a commercially available chewing gum. In this artificial food mass 50, light-transmissive microparticles 54 each having a diameter in a range from about 250 to 300 μm are contained in a substantially black base material 52 serving as a base for the chewing gum. FIG. 4 shows a block-shaped artificial food mass 50. However, the shape of the artificial food mass 50 is not limited, and may have a sheet shape. FIG. 4 illustrates the microparticles 54 with a larger size by a smaller number than actual size and number of the microparticles 54 for explanation.

The base material 52 serving as the base for the chewing gum is not particularly limited, and may be, for example, a black base material, as long as the base material has a property of blocking infrared light. A base material similar to that of a commercially available chewing gum may be used.

Also, the light-transmissive microparticles 54 are not particularly limited as long as the microparticles are harmless even if a human puts the microparticles into his/her mouth. For example, microparticles of carnauba wax may be used.

To evaluate the masticatory function, the artificial food mass 50 is masticated by a human a predetermined number of times, and then the artificial food mass 50 is pressed and sandwiched between the preparation sheets 14, so that an image of the artificial food mass 50 as the imaging object 12 can be captured.

If the artificial food mass 50 uses components equivalent to those of a commercially available chewing gum, various components such as sugar as a sweetener are contained, due to the necessity in a manufacturing process for the chewing gum. Owing to this, the various components contained in the artificial food mass 50 after the artificial food mass 50 is masticated by the human the predetermined number of times are preferably removed by using a various-component removing method.

The various-component removing method may be, for example, kneading the artificial food mass 50 so as not to crush the microparticles 54, or leaving the artificial food mass 50 for a predetermined time while the artificial food mass 50 is sandwiched between cooking sheets (for example, cooking sheets manufactured by Asahi Kasei Home Products Corporation, etc.), and hence removing the various components contained in the artificial food mass 50.

Also, FIG. 5(a) is a brief configuration diagram for explaining a structure of the preparation sheets used for capturing the image of the chewing gum in FIG. 4 by the imaging system of the present invention. FIG. 5(b) is a plan configuration diagram for explaining a state in which the chewing gum is pressed by the preparation sheets. FIG. 6(a) is an A-A sectional view of the preparation sheets in FIG. 5(a). FIG. 6(b) is a sectional view according to another embodiment different from FIG. 6(a).

Figure 5:
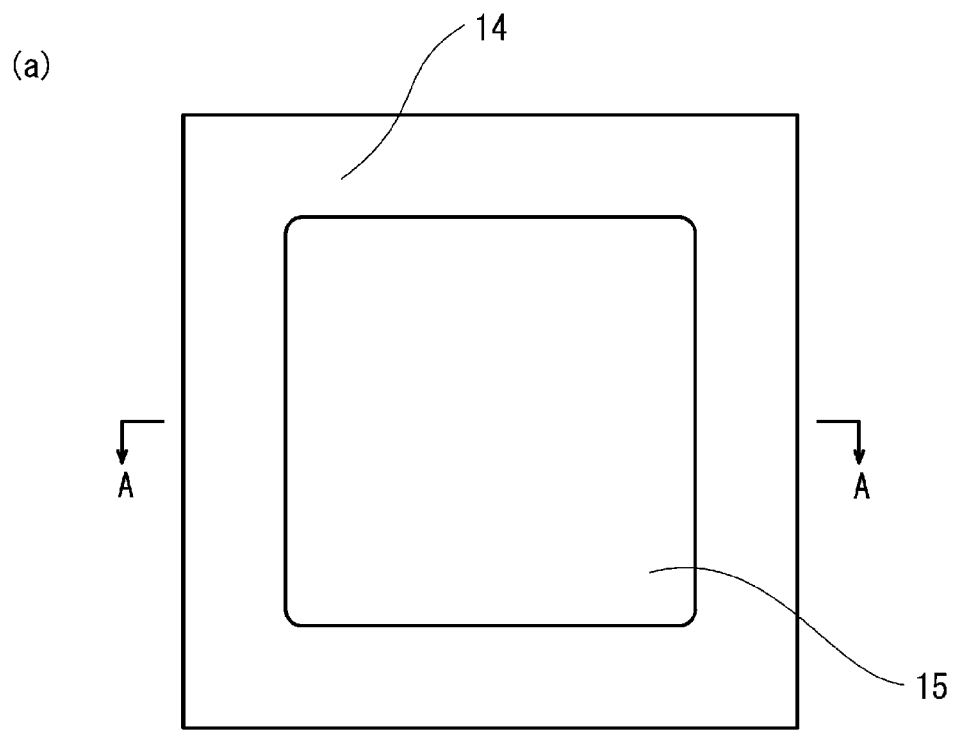
FIG. 5(a) is a brief configuration diagram for explaining a state in which the chewing gum in FIG. 4 is pressed by preparation sheets for capturing the image of the chewing gum by the imaging system of the present invention.
FIG. 5(b) is a plan configuration diagram for explaining the state in which the chewing gum is pressed by the preparation sheets.
Figure 5:
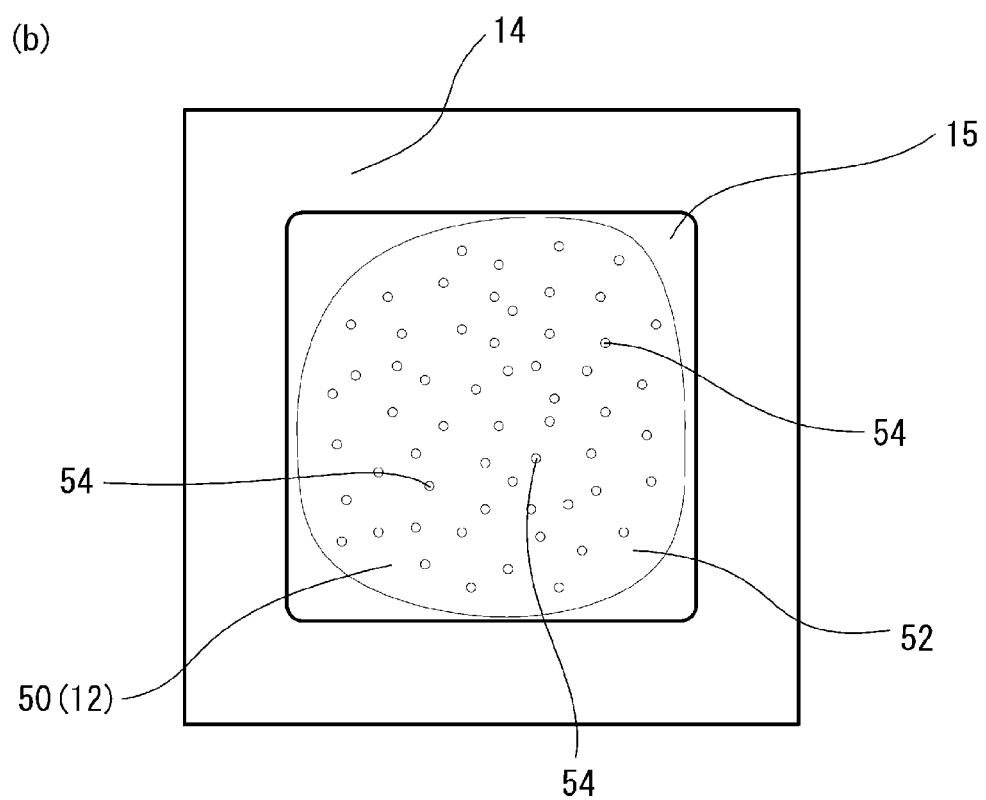

As shown in FIG. 5, the preparation sheets 14 each have a gap adjustment recess 15 so that a gap with a depth that is about 125% of the diameter of the microparticle 54 is formed. The artificial food mass 50 is pressed through the preparation sheets 14 while the artificial food mass 50 is arranged in the gap adjustment recesses 15 of the preparation sheets 14, and the artificial food mass 50 is sandwiched between the preparation sheets 14. Accordingly, as shown in FIG. 5(b), the artificial food mass 50 can be spread so that the microparticles 54 are not overlapped with each other. In FIG. 5, the thickness of the preparation sheet 14 and the depth of the gap adjustment recess 15 are different from those of the actual scales. Also, FIG. 5 illustrates the microparticles 54 with a larger size by a smaller number than actual size and number of the microparticles 54 for explanation.

Figure 6:
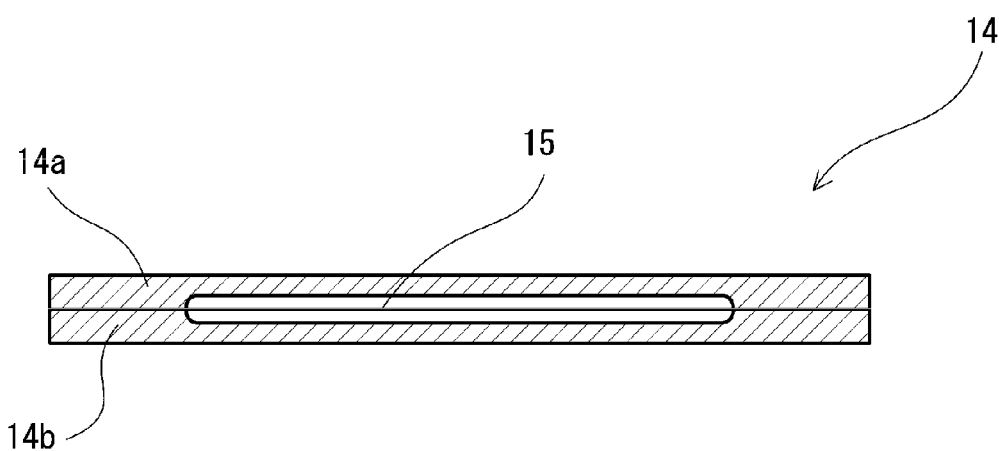
FIG. 6(a) is an A-A sectional view of the preparation sheets in FIG. 5(a).
FIG. 6(b) is a sectional view according to another embodiment different from FIG. 6(a).
Figure 6:
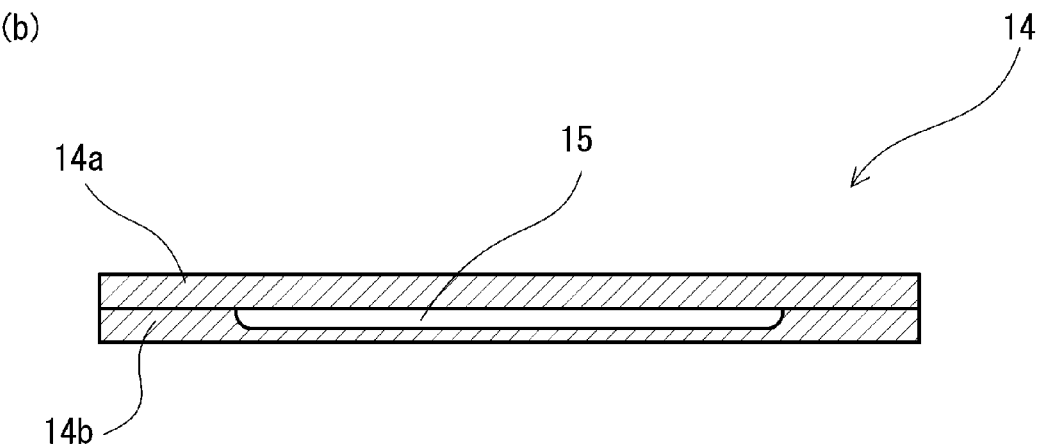

In the preparation sheets 14 shown in FIG. 5 and FIG. 6(a), both an upper preparation sheet 14a and a lower preparation sheet 14b have the gap adjustment recesses 15. However, the gap adjustment recesses 15 are not limited thereto. For example, as shown in FIG. 6(*b*), only the lower preparation sheet 14*b* may have the gap adjustment recess 15.

As described above, the preparation sheets 14 with the artificial food mass 50 serving as the imaging object 12 sandwiched therebetween are arranged at a position above the infrared light source 24 of the imaging system 10 and below the imaging means 22.

Then, while the infrared light source 24 provides the emission, the imaging means 22 captures an image of the imaging object 12. If the imaging means 22 is a digital camera, as described above, captured infrared image data is stored in the storage device 42 of the computer 40. In contrast, if the imaging means 22 is a film camera, a film after image capture is developed, and the developed image is read by an image scanner or the like, the read image is acquired as image data by the computer 40, and the image data is stored in the storage device 42.

Hereinafter, image processing for captured infrared image data is described.

Figure 7:
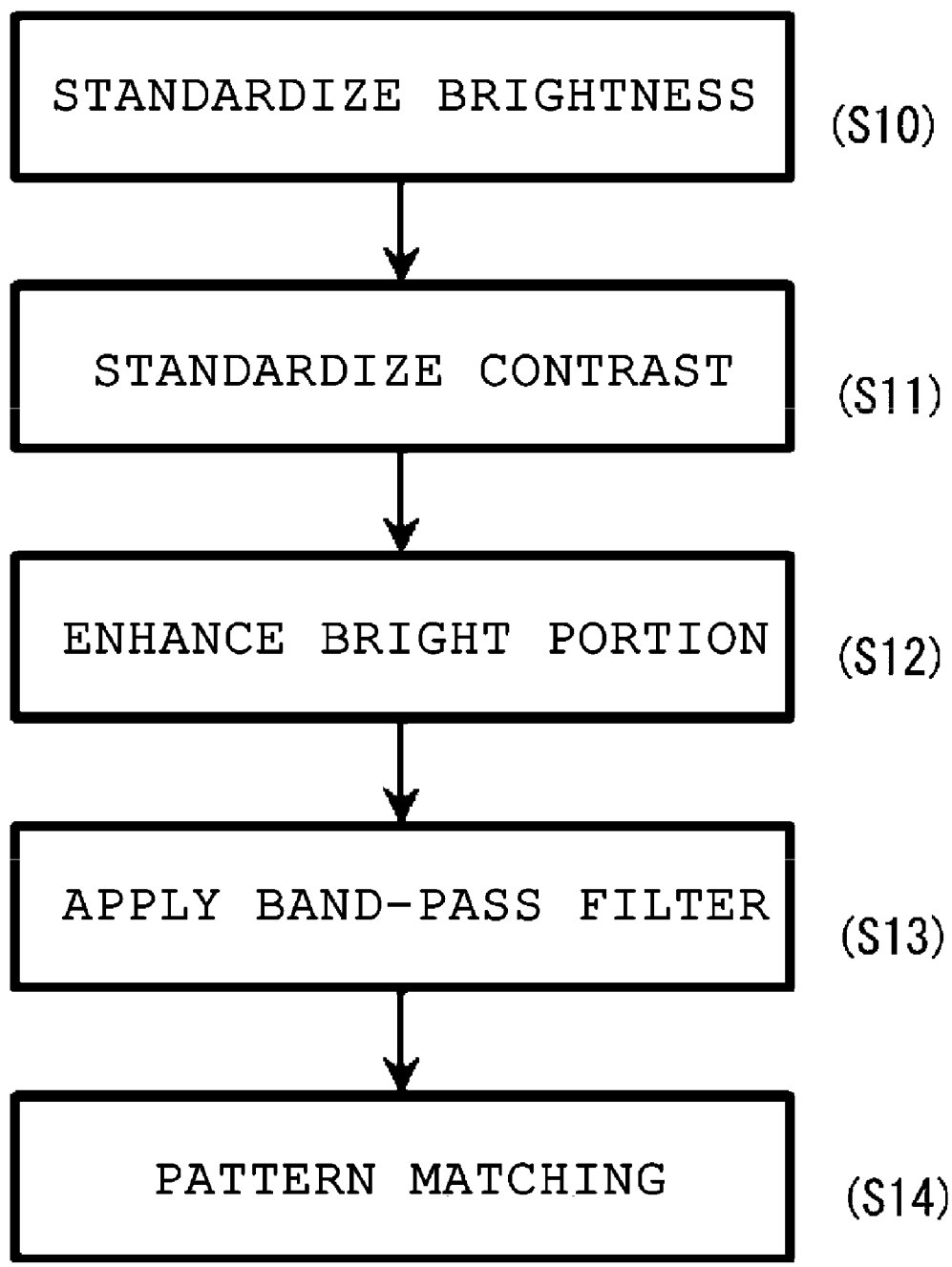
FIG. 7 is a flowchart explaining a flow of image processing for captured infrared image data.

As described above, the infrared image captured by the imaging device 20 is saved as the infrared image data in the storage device 42 of the computer 40. Then, the arithmetic device 44 performs image processing on the saved image data in accordance with a procedure shown in FIG. 7 so that the shapes of the microparticles 54 become clear.

The infrared image data captured by the imaging device 20 is monochromatic (achromatic) image data in which each pixel has only brightness level information. Also.

First, image processing is performed so that the brightness of the infrared image data becomes the brightness of predetermined model image data (S10).

More specifically, a brightness distribution (histogram) of the infrared image data is calculated, and a mathematic operation is performed on the infrared image data so that the maximum value and the average value of brightnesses of the infrared image data become close to the maximum value and the average value of brightnesses of the model image data.

Figure 8:
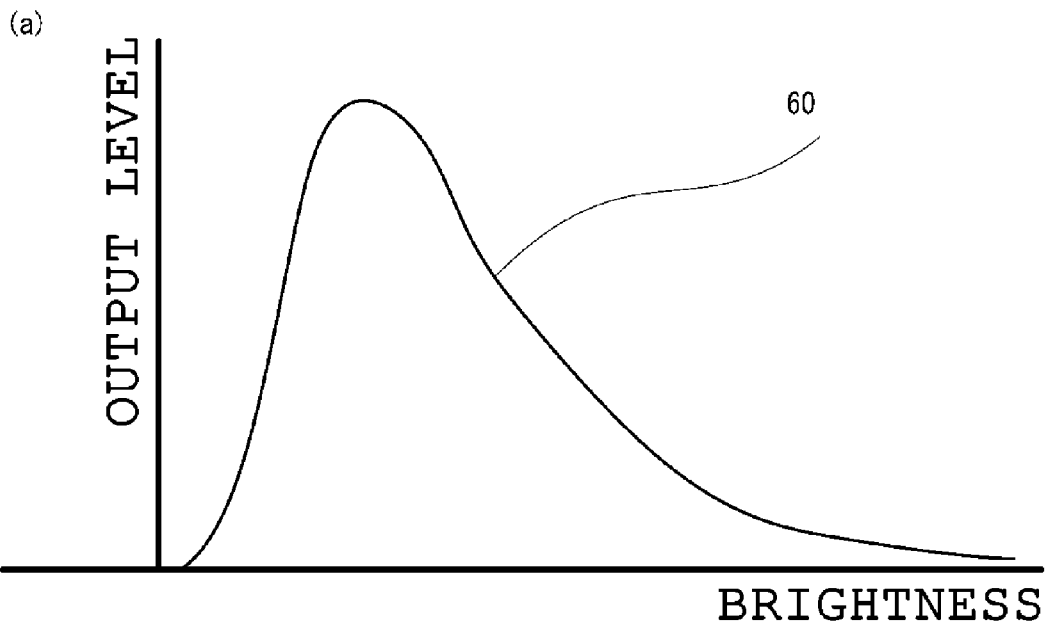
FIG. 8 expresses brightness distributions (histograms) for image data during image processing.
Figure 8:
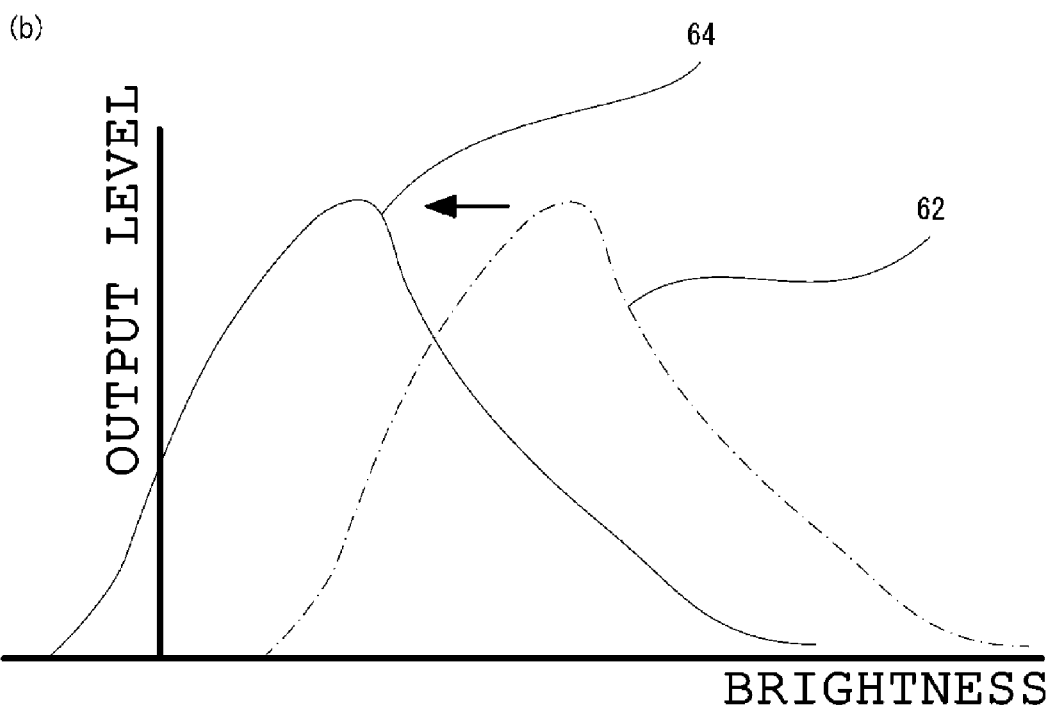

If the brightness distribution (histogram) of the model image data is expressed as a histogram 60 shown in FIG. 8(*a*) and the brightness distribution (histogram) of the captured infrared image data is expressed as a histogram 62 shown in FIG. 8(*b*), the brightness is adjusted so that the maximum value of the brightness of the histogram 62 becomes equivalent to the maximum value of the brightness of the histogram 60.

With this adjustment, the brightness distribution (histogram) of the infrared image data can be expressed as a histogram 64 shown in FIG. 8(*b*). The infrared image after the brightness is adjusted is called brightness-standardized image data.

In the brightness distribution (histogram) of the image data shown in FIG. 8, the horizontal axis plots the brightness and the vertical axis plots the output level. That is, the histogram shown in FIG. 8(*a*) represents that pixels with a low brightness are many (that is, the amount of the base material 52 is large in the imaging object 12) and pixels with a high brightness are few (that is, the number of microparticles 54 is small in the imaging object 12).

Next, image processing is performed so that the contrast of the brightness-standardized image data becomes the contrast of the predetermined model image data (S11).

More specifically, the brightness distribution (histogram) of the brightness-standardized image data is calculated, and a mathematic operation is performed on the brightness-standardized image data so that the standard deviation and dispersion of the brightness-standardized image data become close to the standard deviation and dispersion of the model image data.

Figure 9:
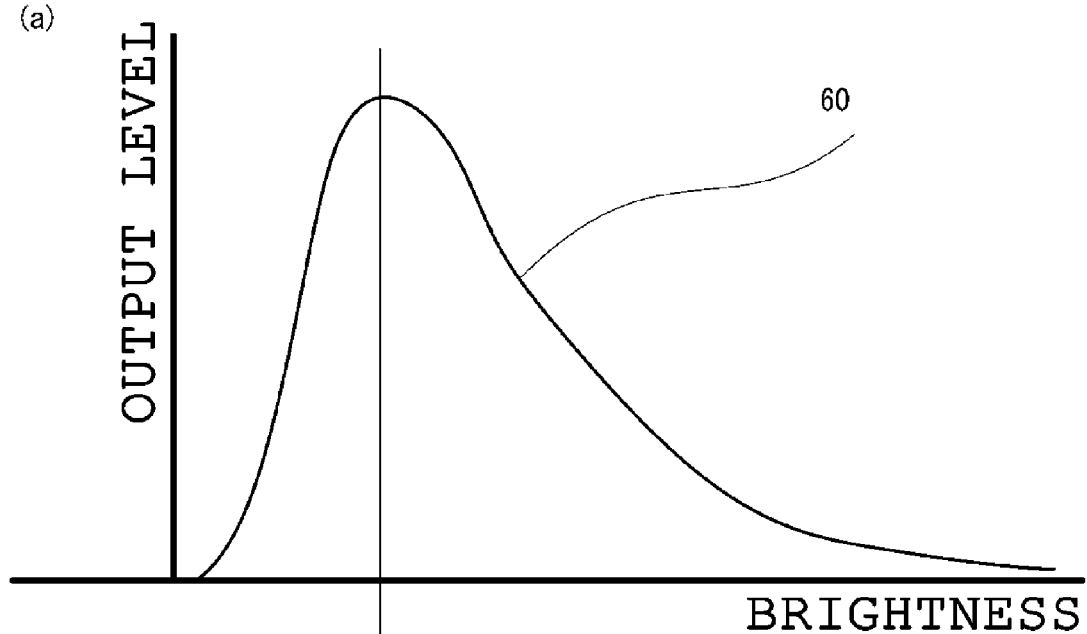
FIG. 9 expresses brightness distributions (histograms) for image data during image processing.
Figure 9:
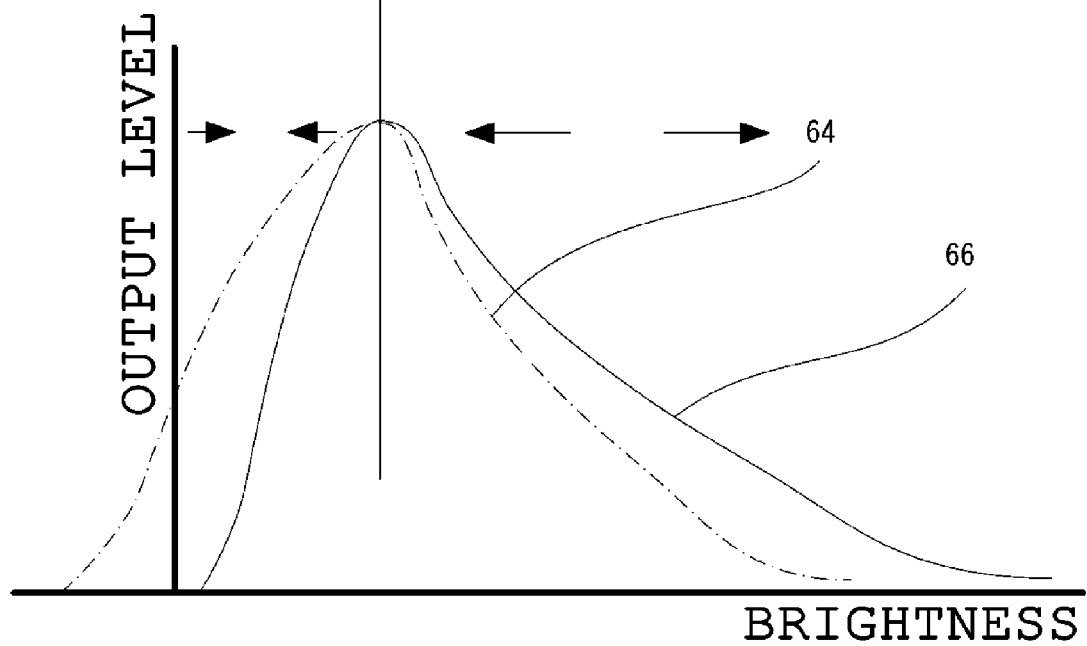

If the brightness distribution (histogram) of the model image data is expressed as a histogram 60 in FIG. 9(*a*), and the brightness distribution (histogram) of the brightness-standardized image data is expressed as a histogram 64 in FIG. 9(*b*), the brightness distribution of the brightness-standardized image data is adjusted so that a bright portion in the histogram 64 is expressed with a small number of gradations and a dark portion in the histogram 64 is expressed with a large number of gradations. That is, the adjustment can be performed by narrowing the dark portion and widening the bright portion while the position of the maximum value of the histogram 64 is not changed. With this adjustment, the brightness distribution (histogram) of the brightness-standardized image data can be expressed as a histogram 66 shown in FIG. 9(*b*). The brightness-standardized image data after the contrast is adjusted is called contrast-standardized image data.

Next, image processing is performed on the contrast-standardized image data so that the difference in brightness between the microparticles 54 (with a high brightness) and the base material 52 (with a low brightness) is increased (S12).

More specifically, the brightness distribution (histogram) of the contrast-standardized image data is calculated, the brightness of a region indicative of the microparticles 54 (i.e., the bright portion) is increased in the brightness distribution of the contrast-standardized image data, and thus the difference in brightness is increased. The contrast-standardized image data after the difference in brightness is adjusted in this way is called enhanced image data.

Next, band-pass filter processing is performed on the enhanced image data. In this processing, the brightness of an edge portion of the microparticle 54 serves as a threshold (S13).

Figure 10:
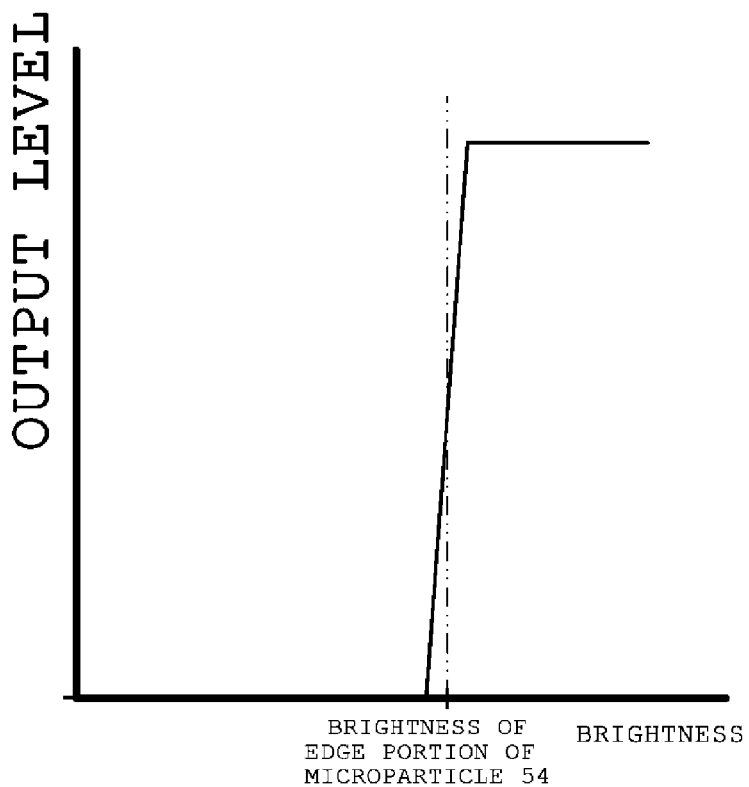
FIG. 10 includes illustrations showing examples of bandpass filters that are applied to enhanced image data.
Figure 10:
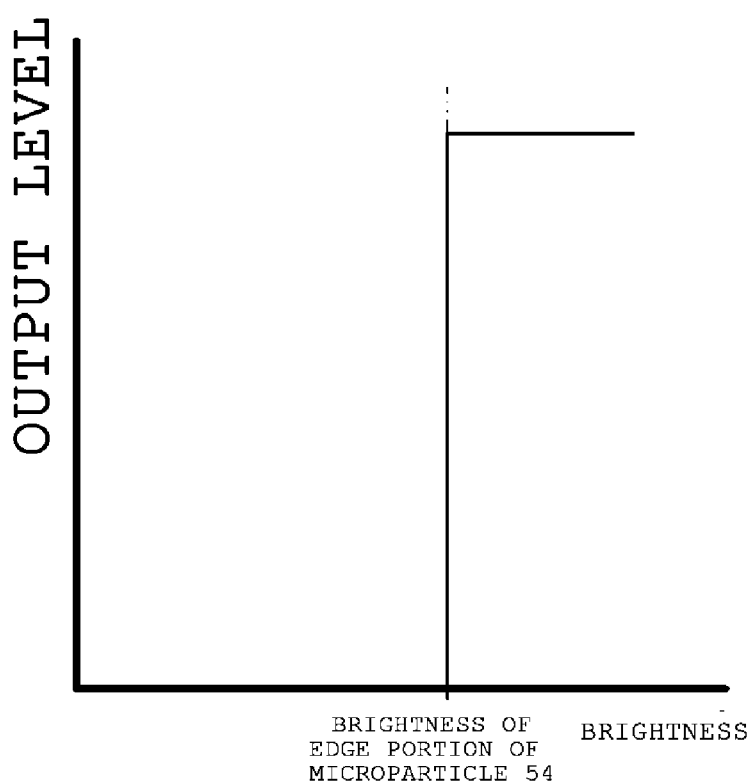

More specifically, a high-pass filter as shown in FIG. 10(*a*) is applied to the enhanced image data. Hence, the brightness of a center portion of the microparticle is treated as the maximum (i.e., white) and the brightness of a base material 52 portion separated from the microparticle is treated as the minimum (i.e., black). Thus, the difference in brightness between the microparticle 54 and the base material becomes further clear. The enhanced image data after the band-pass filter processing is performed in this way is called count image data.

In this embodiment, a high-pass filter having a predetermined inclination is applied for the brightness of the edge portion of the microparticle 54. However, the degree of inclination may be properly set. Also, as shown in FIG. 10(*b*), a binarizing filter for binarization may be applied for the brightness of the edge portion of the microparticle 54.

Figure 11:
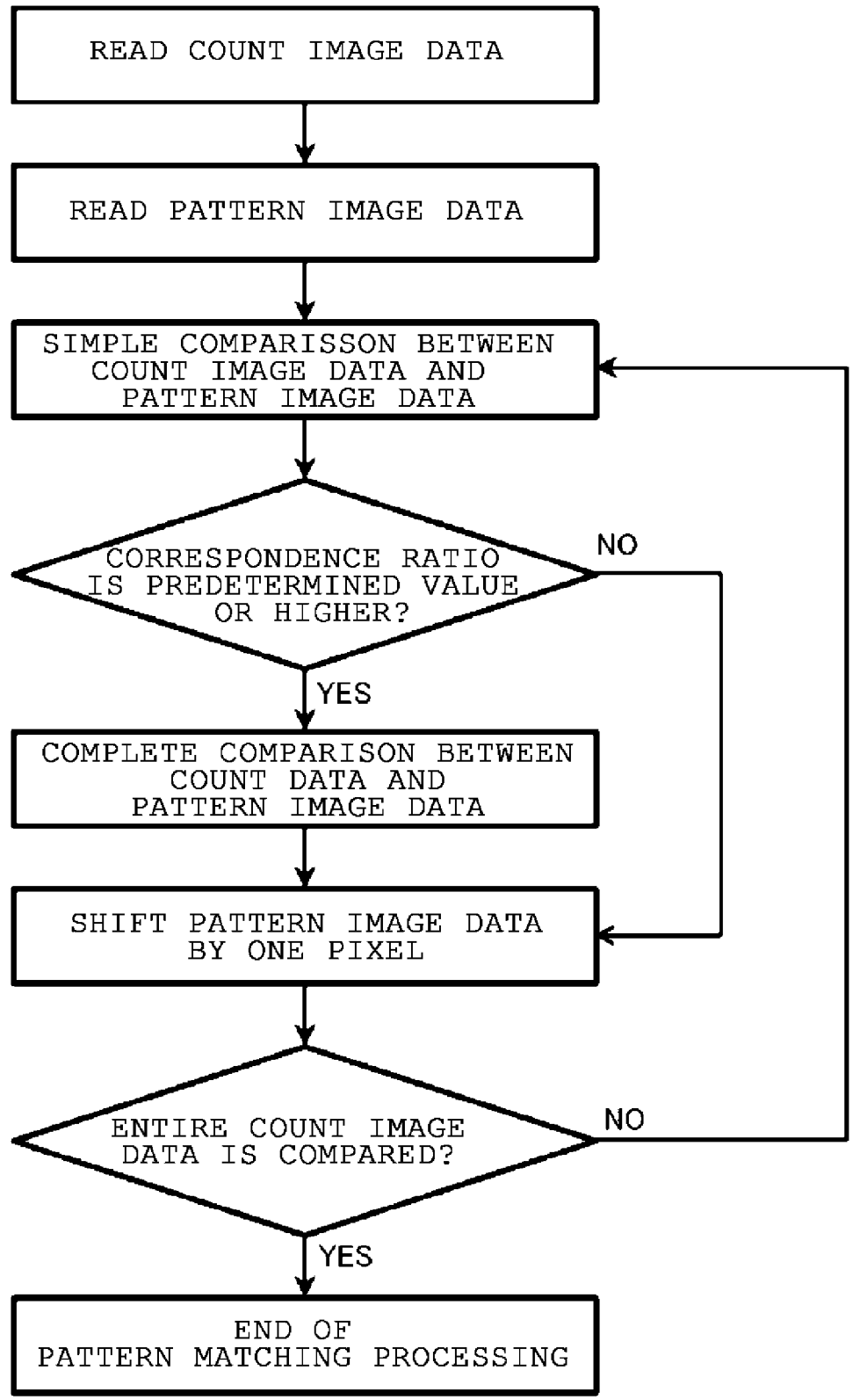
FIG. 11 is a flowchart explaining a flow for performing pattern matching.

As described above, since the shapes of the microparticles 54 become clear, the number of microparticles 54 can be accurately and quickly counted by the arithmetic device 44, for example, by using a method for pattern matching as shown in FIG. 11 (S14).

Figure 12:
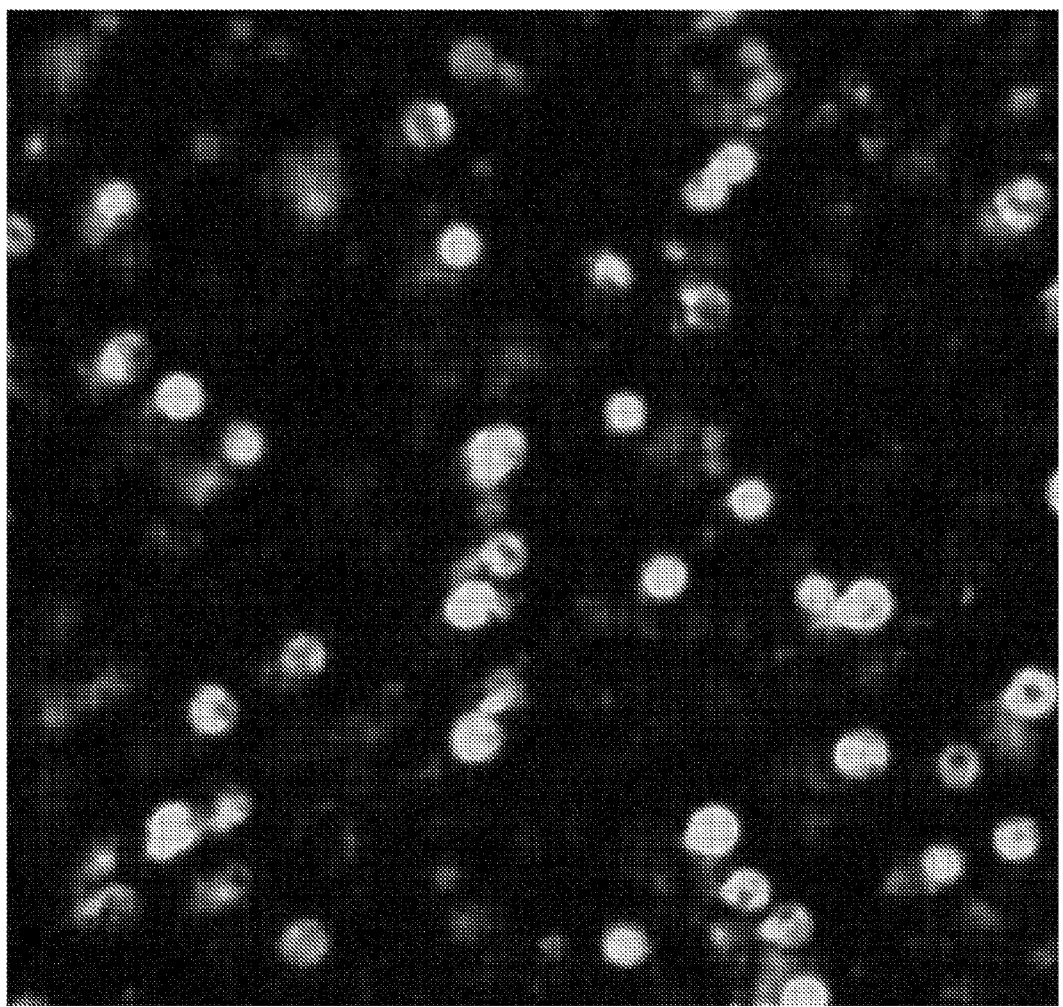
FIG. 12 is an illustration for explaining the pattern matching that is performed for count image data, the illustration showing infrared image data when an image of an imaging object is captured.
Figure 15:
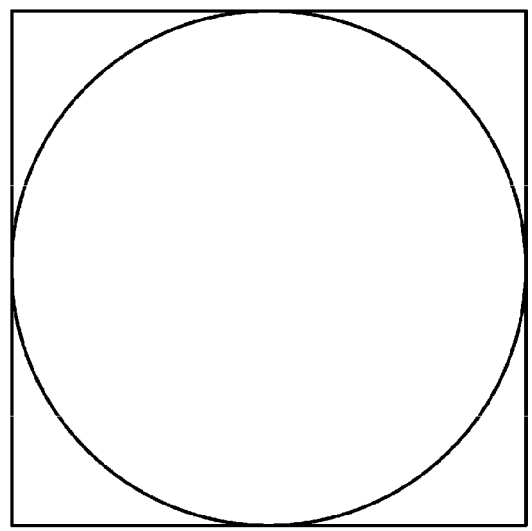
FIG. 15(a) is an illustration showing pattern image data that is a pattern of a shape of a microparticle.
FIG. 15(b) is an illustration showing pixels in the pattern image data that is used in a simple comparison step.
Figure 15:
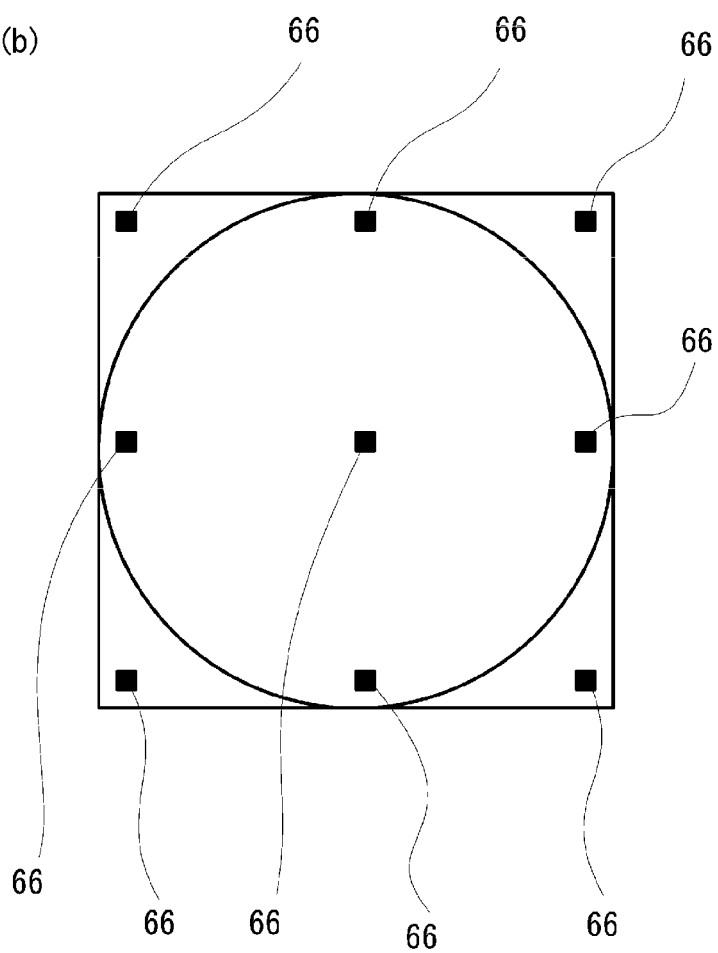

In this embodiment, the method for pattern matching may be performed by the arithmetic device 44 by calculating the correspondence ratios of all pixels while pattern image data in FIG. 15(*a*) is shifted with respect to the count image data in FIG. 12 pixel by pixel. Alternatively, if the following method is used, pattern matching can be performed more quickly.

FIG. 11 is a flowchart explaining a flow for performing pattern matching quickly.

For example, if the above-described image processing is performed on infrared image data captured as shown in FIG.

Figure 13:
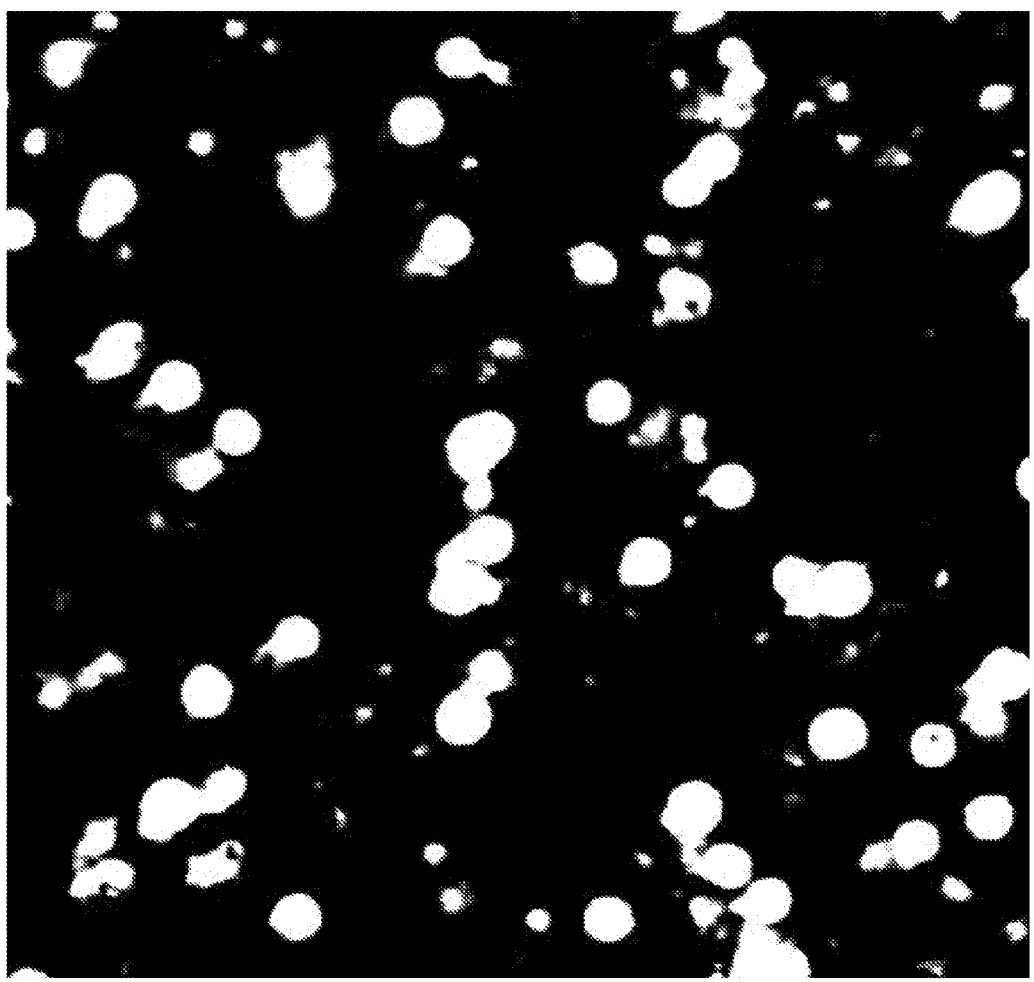
FIG. 13 is an illustration for explaining the pattern matching that is performed for the count image data, the illustration showing the count image data for performing the pattern matching.

12, count image data as shown in FIG. 13 is obtained. If one pixel in the count image data corresponds to 10 μm, pattern image data in FIG. 15(a) may have, for example, a shape in which a white circle with a diameter of 28 pixels (i.e., with the maximum brightness) is drawn in a black square with a side length of 28 pixels (i.e., with the minimum brightness) (28-pixel pattern image).

To perform the pattern matching, the arithmetic device 44 of the computer 40 reads the count image data and the pattern image data, and matches the pattern image data with the count image data at a start position (at an upper left position of the image data).

After the matching, the pattern image data is shifted rightward on the count image data by only one pixel, and the matching is performed again. This process is repeated. If the pattern image data reaches the right end on the count image data, the pattern image data is shifted downward by only one pixel on the count image data, the pattern image data is moved to the left end, and the pattern matching is continued.

Figure 14:
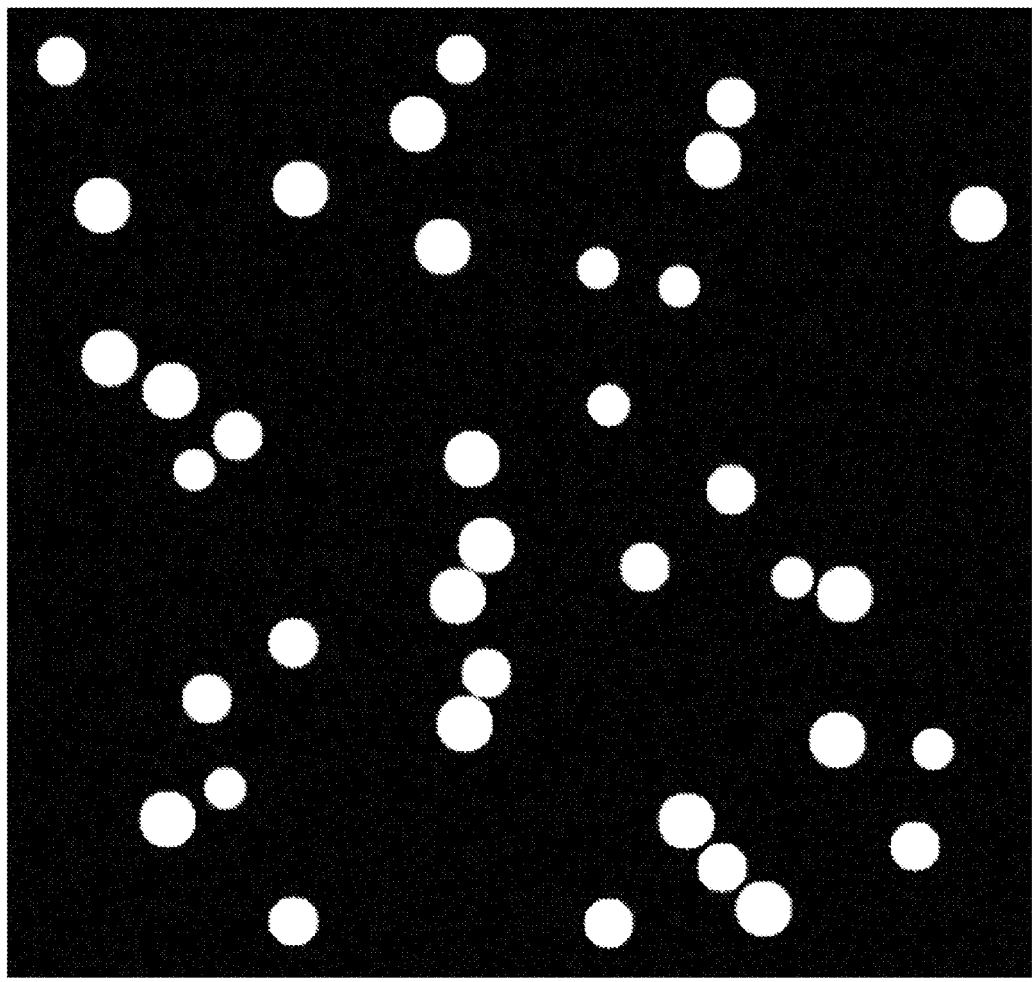
FIG. 14 is an illustration for explaining the pattern matching that is performed for the count image data, the illustration showing a result of the pattern matching.

In this way, the matching is repeated until the pattern image data reaches an end position of the count image data (a lower right position of the image data). Accordingly, as shown in FIG. 14, the "particles not finely crushed or ground" can be matched and counted.

When the matching is performed, as shown in FIG. 15(b), the correspondence ratios of only 9 pixels 66 in total at the center and edge portions of the pattern image data may be calculated by the arithmetic device 44 (simple comparison step), and if the correspondence ratios are higher than a constant value, all pixels in the pattern image data may be calculated by the arithmetic device 44 (complete comparison step). Accordingly, the speed of the pattern matching can be increased, and the accuracy of the pattern matching can be ensured.

The correspondence ratio may be properly set. If the correspondence ratio is about 80% or higher, the microparticles 54 can be accurately judged.

The pattern matching may be performed by using a plurality of kinds of pattern image data. In this case, the pattern matching is performed as described above successively with the plurality of kinds of pattern image data. Then, an average value of the results is calculated. Hence, the number of microparticles can be further accurately counted.

If the microparticles 54 with diameters in a range from 250 to 300 μm are used like this embodiment, the pattern matching may be performed preferably with use of three kinds of pattern image data including 32-pixel pattern image, 28-pixel pattern image, and 24-pixel pattern image.

As shown in FIG. 12, if an image of the entire imaging object 12 cannot be captured because of problems in the number of effective pixels and resolution of the imaging means 22, by mounting the preparation sheets 14 on a base that is rotatable in the plane direction and by capturing an image by the imaging means 22 while rotating the preparation sheets 14, the image of the imaging object 12 can be captured while the focal distance etc. of the imaging means 22 is not changed.

The preferred embodiment of the present invention is described above. However, the present invention is not limited thereto, and various modifications can be made without departing from the objects of the present invention. For example, the computer 40 that performs the image processing may serve as a server, image data captured by the imaging device 20 may be transmitted to the server through a network such as the internet, and image processing may be performed.

REFERENCE SIGNS LIST 10 imaging system
12 imaging object
14 preparation sheet
15 gap adjustment recess
20 imaging device
22 imaging means
24 infrared light source
25 mount table
26 visible-light cut filter
28 diffusing filter
30 holding means
32 support shaft
34 base portion
36 cable
40 computer
42 storage device
44 arithmetic device
50 artificial food mass
52 base material
54 microparticle
60 histogram
62 histogram
64 histogram
66 histogram

The invention claimed is:

1. An imaging method for capturing an image of an artificial food mass, in which a light-transmissive microparticle is contained in a base material having a property of blocking infrared light, by an imaging device for capturing an image of an imaging object that is an artificial food mass, in which a light-transmissive microparticle is contained in a base material having a property of blocking infrared light, the imaging device comprising:
imaging means for capturing the image of the imaging object from one side; and
an infrared light source that emits infrared light on the imaging object from the other side of the imaging object,
wherein the imaging means includes visible-light removing means for not receiving visible light, and
wherein the imaging means captures the image of the imaging object while the infrared light source emits the infrared light on the imaging object, and
wherein the method comprising:
after the artificial food mass is masticated by a human a predetermined number of times, emitting the infrared light from the infrared light source on the artificial food mass from one side of the artificial food mass, and capturing the image of the artificial food mass by the imaging means from the other side of the artificial food mass, while the artificial food mass is sandwiched between the preparation sheets.

2. An imaging method for capturing an image of a chewing gum, in which a light-transmissive microparticle is contained in a base material having a property of blocking infrared light, by an imaging device for capturing an image of an imaging object that is an artificial food mass, in which a light-transmissive microparticle is contained in a base material having a property of blocking infrared light, the imaging device comprising:
imaging means for capturing the image of the imaging object from one side; and
an infrared light source that emits infrared light on the imaging object from the other side of the imaging object,
wherein the imaging means includes visible-light removing means for not receiving visible light, and
wherein the imaging means captures the image of the imaging object while the infrared light source emits the infrared light on the imaging object, and wherein the method comprising:
   after the chewing gum is masticated by a human a predetermined number of times, removing various components by using a various-component removing method for removing the various components contained in the chewing gum; and
   emitting the infrared light from the infrared light source on the artificial food mass from one side of the artificial food mass, and capturing the image of the artificial food mass by the imaging means from the other side of the artificial food mass, while the chewing gum is sandwiched between the preparation sheets.

3. The imaging method according to claim 2, wherein the various-component removing method is one of kneading in warm water and sandwiching between cooking sheets for a predetermined time.

4. An image processing method for causing a shape of the microparticle to be clear in the image of an imaging object captured by an imaging device for capturing an image of an imaging object that is an artificial food mass, in which a light-transmissive microparticle is contained in a base material having a property of blocking infrared light,
   the imaging device comprising:
   imaging means for capturing the image of the imaging object from one side; and
   an infrared light source that emits infrared light on the imaging object from the other side of the imaging object,
   wherein the imaging means includes visible-light removing means for not receiving visible light, and
   wherein the imaging means captures the image of the imaging object while the infrared light source emits the infrared light on the imaging object, and
   wherein the method comprising:
   a step of performing a mathematic operation on image data and generating brightness-standardized image data so that a brightness of the captured image data becomes close to a brightness of predetermined model image data;
   a step of performing a mathematic operation on the brightness-standardized image data and generating contrast-standardized image data so that a contrast of the brightness-standardized image data becomes close to a contrast of the model image data;
   a step of calculating a brightness distribution of the contrast-standardized image data, performing a mathematic operation on the contrast-standardized image data, and generating enhanced image data so that a brightness of a region indicative of the microparticle is increased in the brightness distribution; and
   a step of applying a band-pass filter, in which a brightness of an edge portion of the microparticle is a threshold, to the enhanced image data, and generating count image data.

5. The image processing method according to claim 4, wherein the microparticle includes a plurality of microparticles, and the number of the microparticles in the count image data is counted by comparing the count image data with pattern image data indicative of a shape of the microparticle.

6. The image processing method according to claim 5, comprising:
   a simple comparison step of comparing only a predetermined number of pixels in a region indicative of the shape of the microparticle in the pattern image data and a predetermined number of pixels outside the region indicative of the shape of the microparticle, with the count image data; and
   a complete comparison step of comparing all pixels in the pattern image data with the count image data if a result of the simple comparison step exceeds a predetermined correspondence ratio.

7. An imaging system, comprising: an imaging device for capturing an image of an imaging object; and an image processing device for processing image data of the imaging object that is an artificial food mass, in which a light-transmissive microparticle is contained in a base material having a property of blocking infrared light, captured by the imaging device,
   the imaging device comprising:
   imaging means for capturing the image of the imaging object from one side; and
   an infrared light source that emits infrared light on the imaging object from the other side of the imaging object,
   wherein the imaging means includes visible-light removing means for not receiving visible light, and
   wherein the imaging means captures the image of the imaging object while the infrared light source emits the infrared light on the imaging object, and
   wherein the image processing device includes
   a storage device for saving the image data captured by the imaging device, and
   an arithmetic device for processing the image data saved in the storage device, and
   wherein the image processing device
   performs a mathematic operation on the image data and generates brightness-standardized image data so that a brightness of the captured image data becomes close to a brightness of predetermined model image data,
   performs a mathematic operation on the brightness-standardized image data and generates contrast-standardized image data so that a contrast of the brightness-standardized image data becomes close to a contrast of the model image data,
   calculates a brightness distribution of the contrast-standardized image data, performs a mathematic operation on the contrast-standardized image data, and generates enhanced image data so that a brightness of a region indicative of the microparticle is increased in the brightness distribution, and
   applies a band-pass filter, in which a brightness of an edge portion of the microparticle is a threshold, to the enhanced image data, and generates count image data.

8. The imaging system according to claim 7, wherein the microparticle includes a plurality of microparticles, and the number of microparticles in the count image data is counted by comparing the count image data with pattern image data indicative of s shape of the microparticle.

9. The imaging system according to claim 8, comprising:
   a simple comparison step of comparing only a predetermined number of pixels in a region indicative of the shape of the microparticle in the pattern image data and a predetermined number of pixels outside the region indicative of the shape of the microparticle, with the count image data; and
   a complete comparison step of comparing all pixels in the pattern image data with the count image data if a result of the simple comparison step exceeds a predetermined correspondence ratio.

* * * * *